US00PP18731P2

(12) United States Plant Patent
McCracken

(10) Patent No.: US PP18,731 P2
(45) Date of Patent: Apr. 15, 2008

(54) ***MYRICA* PLANT NAMED 'SOLEIL '**

(50) Latin Name: *Myrica cerifera*
Varietal Denomination: SOLEIL

(76) Inventor: T. Patrick McCracken, 8025 Fowler Rd., Zebulon, NC (US) 27597

( * ) Notice: Subject to any disclaimer, the term of this patent is extended or adjusted under 35 U.S.C. 154(b) by 0 days.

(21) Appl. No.: 11/512,618

(22) Filed: Aug. 29, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—S. B. McCormick-Ewoldt

(57) ABSTRACT

A new cultivar of *Myrica* plant named 'SOLEIL' that is characterized by densely branched, brilliant yellow foliage. In combination these traits set 'SOLEIL' apart from all other exiting varieties of *Myrica* known to the inventor.

3 Drawing Sheets

Genus: Myrica.
Species: *cerifera.*
Denomination: SOLEIL.

BACKGROUND OF THE INVENTION

The present invention relates to a new and distinct cultivar of *Myrica* or wax myrtle that is grown for use as an ornamental evergreen shrub or small tree. It is known botanically as *Myrica cerifera* and will be referred to hereinafter by the cultivar name 'SOLEIL'.

'SOLEIL' is the product of a breeding program started by the inventor in 1992 in a cultivated area of Raleigh, N.C. The primary focus of the breeding program is to produce new cultivars of shrubs and trees with attractive foliage.

'SOLEIL' was selected in 1994 as a single seedling from a large population of seedlings which the inventor had grown from seed collected from pollination of the inventor's large collection of *Myrica.* The inventor is unable to identify either the male or the female parent.

'SOLEIL' exhibits brilliant yellow foliage. There are no known comparable cultivars known to the inventor. There are varieties that are unique for dwarfness or cut leaves including *Myrica* 'Georgia Gem' (U.S. Plant Pat. No. 6,411) and *Myrica* 'Lane' (U.S. Plant Pat. No. 7,555), but these do not exhibit the bright gold-yellow leaf color of 'Soleil'.

Asexual reproduction of the new cultivar was first accomplished by the inventor in 1994 in a cultivated area of Raleigh, N.C. The method of asexual propagation used was softwood cuttings. Since that time the characteristics of the new cultivar have been determined stable and are reproduced true to type in successive generations by asexual propagation.

SUMMARY OF THE INVENTION

The following traits have been repeatedly observed and represent the characteristics of the new *Myrica* cultivar 'SOLEIL'. These traits in combination distinguish 'SOLEIL' from all other varieties of *Myrica* known to the inventor. 'SOLEIL' has not been tested under all possible conditions and phenotypic differences may be observed with variations in environmental, climatic and cultural conditions, without however any change in genotype.

1. *Myrica* 'SOLEIL' exhibits a densely branched shrub, round in shape.
2. *Myrica* 'SOLEIL' exhibits brilliant yellow foliage.
3. *Myrica* 'SOLEIL' is 2 m in height and 3 m in wide at 7 years.
4. *Myrica* 'SOLEIL' blooms in late April.
5. *Myrica* 'SOLEIL' is hardy to USDA Hardiness Zone 7.

BRIEF DESCRIPTION OF THE DRAWINGS

The accompanying color drawings illustrate the overall appearance of the new *Myrica* variety 'SOLEIL' showing colors as true as it is reasonably possible to obtain in colored reproductions of this type. Colors in the drawings may differ from the color values cited in the detailed botanical description, which accurately describe the actual colors of the new variety 'SOLEIL'.

Figure 1:
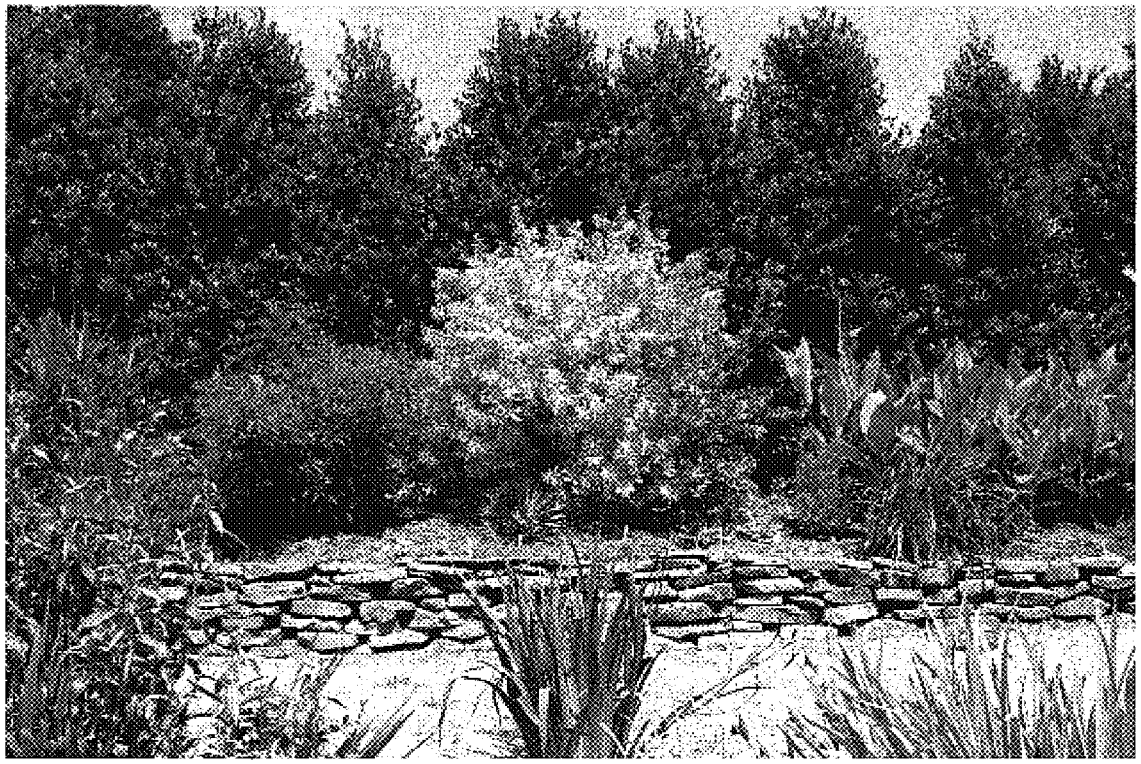
FIG. 1 shows a six year old plant of 'Soleil' which has been established in the landscape in North Carolina. The photograph was taken in mid June and shows the golden foliage of 'Soleil' unaffected by high summer temperatures and light.
Figure 2:
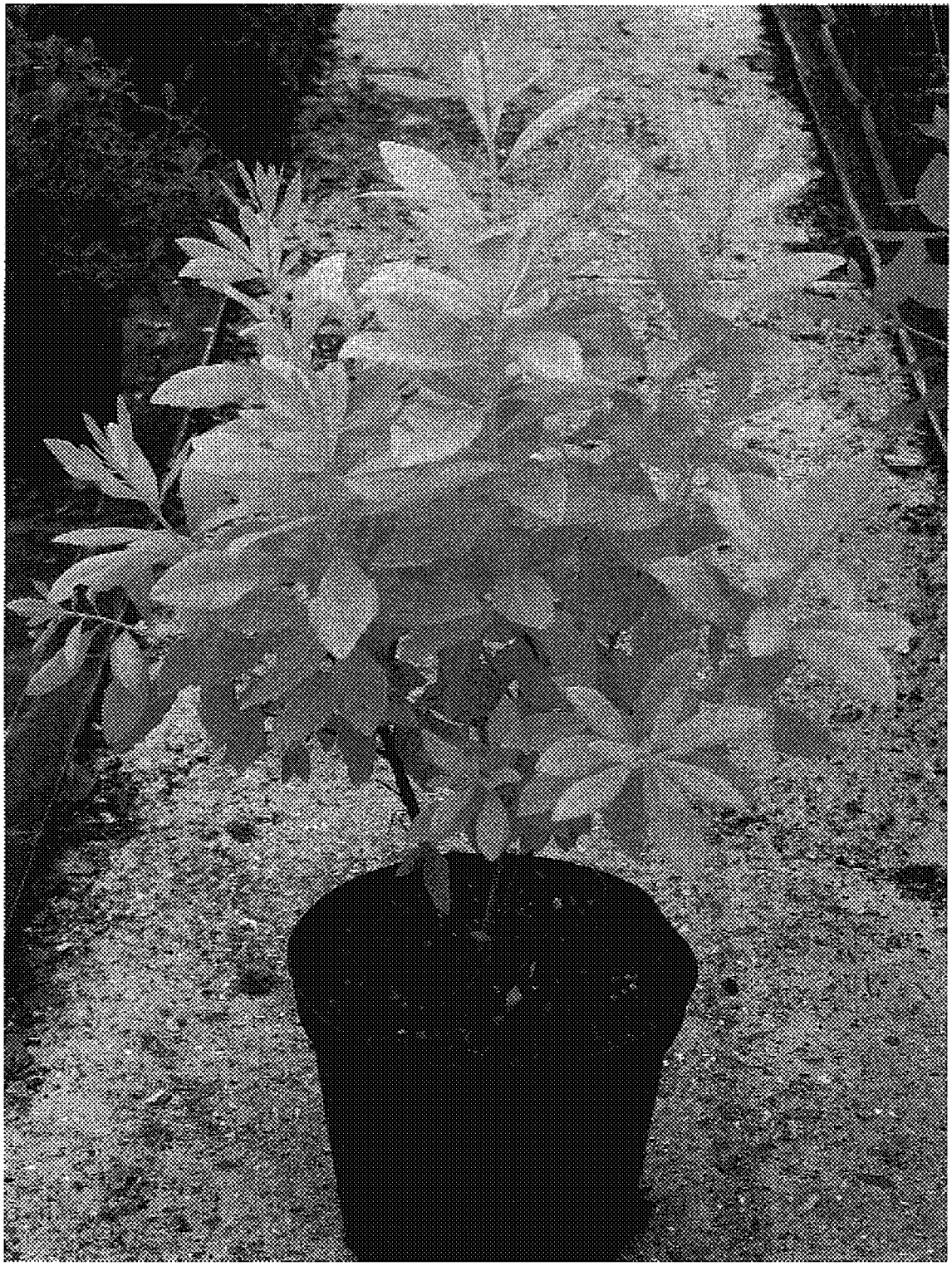
FIG. 2 shows a two year old plant of 'Soleil' which is growing in a 3 gallon container. The plant has been grown in a frost-free greenhouse and the photograph was taken in May.
Figure 3:
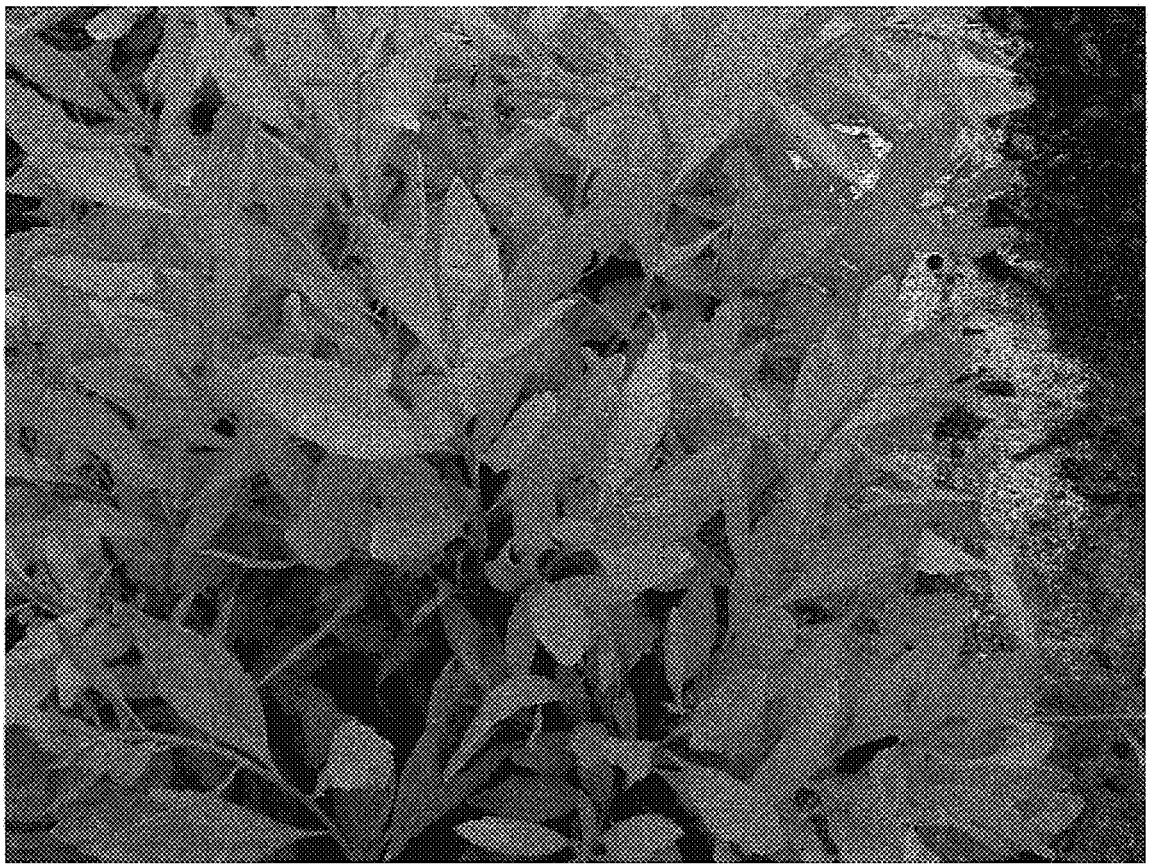
FIG. 3 shows a close up view of the foliage of 'Soleil'.

All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'SOLEIL'. Data was collected from plants grown in out of doors in Raleigh, N.C. The color determinations are in accordance with the 2001 edition of The Royal Horticultural Society Colour Chart of the Royal Horticultural Society, London, England, except where general color terms of ordinary dictionary significance are used. No chemicals were used to treat the plants. Growing conditions are typical to other *Myrica*.

Botanical classification: *Myrica*.
Species: *cerifera*.
Common name: Wax myrtle.
Commercial classification: Evergreen shrub.
Use: Landscape plant.
Parentage:
*Female parent plant*.—Unknown.
*Male parent plant*.—Unknown.
Plant description:
*Plant habit*.—Densely branched shrub, round in shape, but can be sheared into any shape; can be limbed up into multi-trunked small tree.
*Plant dimensions*.—3 m in height and 2 m in width at seven years age.
*Plant hardiness*.—USDA Zone 7b; hardy to 5° Fahrenheit.
*Type*.—Evergreen shrub.
*Root system*.—Fibrous.
*Propagation*.—Propagation is accomplished using stem cuttings.
*Cultural requirements*.—Nothing special — any well drained nursery medium will work.
*Diseases and pests*.—Folia black spot can be a problem when being irrigated overhead but is easily controlled with fungicide. No problems when grown in the ground without overhead irrigation.
*Time required to produce a rooted cutting*.—3–5 weeks are needed to produce a rooted cutting.
*Temperature recommended for cuttings to produce roots*.—The air temperature needed to produce a rooted cutting, is a minimum of 15° Centigrade, and a base heat of 21° Centigrade.
*Crop time*.—1 year is needed to produce a finished 3 gallon plant; 2 years is needed to produce a 5–10 gallon plant from a well-rooted cutting.
Stem:
*Shape*.—Round.
*Stem length* (*main stem*).—At least 750 mm in length.
*Stem length* (*secondary stems*).—7 cm to 30 cm.
*Stem width*.—2 mm.
*Stem surface*.—Glabrous and glaucous.
*Stem* (*twigs*) *color*.—1B maturing to 22A.
*Stem color*.—198D.
*Branching*.—Somewhat sympodial.
*Internode length*.—3 mm to 15 mm.
*Stem surface*.—Short pubescence, less than 1 mm.
*Pubescence color*.—Tan-white to tawny to orange-yellow in color; short floccose.
Foliage:
*Arrangement*.—Alternate.
*Quantity of leaves per stem*.—At least 50.
*Division*.—Simple.
*Shape*.—Narrowly elliptic to oblanceolate.
*Leaf dimensions* (*immature*).—3.5 cm to 5.5 cm in length: 0.7 cm to 1.4 cm in width.
*Leaf dimensions* (*mature*).—5.5 cm to 8 cm in length; 1.5 cm to 2.0 cm in width.
*Leaf tip*.—Acute in shape; submucronate at apex.
*Leaf base*.—Attenuate.
*Margin type*.—Serrate, but only above middle of leaf.
*Leaf surface* (*adaxial*).—Glabrous except along midrib which is slightly pubescent; adaxial surface dotted with sunken punctuate glands, highly pungent when bruised.
*Leaf surface* (*abaxial*).—Abaxial surface studded with raised punctate resinous glands, highly pungent when bruised; midrib has scale-like to glandular trichomes.
*Leaf color* (*immature, adaxial*).—151B to 153B.
*Leaf color* (*immature, abaxial*).—153D.
*Leaf color* (*mature, adaxial*).—144A.
*Leaf color* (*mature, abaxial*).—146B.
*Leaf venation pattern*.—Pinnate.
*Vein color* (*abaxial and adaxial*).—1C.
*Attachment*.—Petiolate.
*Petiole length* (*newer leaves*).—2.5 mm to 4.5 mm.
*Petiole length* (*older leaves*).—3 mm to 6 mm.
*Petiole diameter*.—0.75 mm to 1 mm.
*Petiole shape*.—Flat above; round abaxially.
*Petiole surface*.—Somewhat covered in scale-like, glandular trichomes; otherwise glabrous.
*Petiole color*.—1C.
Flowers:
*Inflorescence form*.—Axillary-borne racemes.
*Flower arrangement*.—Spirally along raceme.
*Quantity of flowers per inflorescence*.—Approximately 12.
*Quantity of flowers per plant*.—Numerous.
*Time and duration of flowering*.—Late winter to early spring; present 1 to 2 weeks.
*Flower*.—Dimensions: 3–4 mm in height and 3–4 mm in diameter. Bud: Shape: Ovoid to ovoid-conical. Color: 6A and 7A. Surface: Short puberulent, pilose, glandular. Dimensions: Approximately 1 mm in length and approximately 1 mm in diameter. Corolla: Apetalous. Petals: Apetalous. Attachment: Sessile. Calyx: Asepalous. Sepals: Asepalous Bracts: Subtending flower. Number: 1. Color (abaxial and adaxial): 6A and 7A. Surface (adaxial): Densely ciliate margins. Surface (abaxial): Densely punctate glandular.
Reproductive Organs:
*Pistil*.—Species is dioecious and has staminate flowers only.
*Number of stamens*.—4 to 5 per flower.
*Stamens, fused or unfused at base*.—Unfused.
*Stamens dimensions*.—1 mm in length and less than 0.5 mm in width.
*Filament color*.—6A and 7A.
*anther shape*.—Elliptic to oblong.
*Anther dimensions*.—Less than 1 mm in length and less than 0.5 mm in width.
*Anther color*.—6A and 7A.
*Pollen color*.—6A and 7A.
*Pollen quantity*.—Plentiful and abundant.
Seeds: None produced; staminate flowers only.

It is claimed:

1. A new and distinct cultivar of *Myrica* plant named 'SOLEIL' as described and illustrated herein.

* * * * *